United States Patent
Joo (10) Patent No.: US 11,167,110 B2
(45) Date of Patent: Nov. 9, 2021

(54) STEERABLE CATHETER

(71) Applicant: IMEDICOM, Gunpo-si (KR)

(72) Inventor: Don Soo Joo, Gunpo-si (KR)

(73) Assignee: IMEDICOM, Gunpo-si (KR)

( * ) Notice: Subject to any disclaimer, the term of this patent is extended or adjusted under 35 U.S.C. 154(b) by 175 days.

(21) Appl. No.: 16/492,881

(22) PCT Filed: Mar. 26, 2018

(86) PCT No.: PCT/KR2018/003497
§ 371 (c)(1),
(2) Date: Sep. 10, 2019

(87) PCT Pub. No.: WO2018/186615
PCT Pub. Date: Oct. 11, 2018

(65) Prior Publication Data
US 2020/0069914 A1 Mar. 5, 2020

(30) Foreign Application Priority Data
Apr. 3, 2017 (KR) ........................ 10-2017-0043153

(51) Int. Cl.
*A61M 25/01* (2006.01)
(52) U.S. Cl.
CPC .... *A61M 25/0147* (2013.01); *A61M 25/0136* (2013.01); *A61M 2025/015* (2013.01)
(58) Field of Classification Search
CPC .......... A61M 25/0147; A61M 25/0133; A61M 2025/015; A61M 25/0105; A61M 25/0144; A61B 18/1492
See application file for complete search history.

(56) References Cited

U.S. PATENT DOCUMENTS 5,399,164 A * 3/1995 Snoke ................... A61M 25/01
604/264
5,891,088 A 4/1999 Thompson et al.
6,030,360 A 2/2000 Biggs
(Continued)

FOREIGN PATENT DOCUMENTS

| JP | H1033688 A | 2/1998 |
| JP | 2009530051 A | 8/2009 |
| KR | 1020140099713 A | 8/2014 |

*Primary Examiner* — Bhisma Mehta
*Assistant Examiner* — Neeraja Gollamudi
(74) *Attorney, Agent, or Firm* — Rabin & Berdo, P.C.

(57) ABSTRACT

The technical objective of the present disclosure is to provide a steerable catheter enabling a lumen tip to approach an affected area only with an endoscope inserted together, without the aid of a C-type gantry based tomography apparatus. To this end, the steerable catheter according to the present disclosure includes: a housing; a lumen shaft; upper left, lower left, upper right and lower right wire parts; upper left, lower left, upper right and lower right stoppers; and a steering part for upwardly steering the terminal end of the lumen shaft by pulling the upper left and upper right wire parts, downwardly steering the terminal end of the lumen shaft by pulling the lower left and lower right wire parts, leftwardly steering the terminal end of the lumen shaft by pulling the upper left or lower left wire part, and rightwardly steering the terminal end of the lumen shaft by pulling the upper right or lower right wire part.

8 Claims, 10 Drawing Sheets

(56) References Cited

U.S. PATENT DOCUMENTS

| | | | |
|---|---|---|---|
| 2006/0252993 A1* | 11/2006 | Freed | A61M 25/0147 600/146 |
| 2010/0069834 A1* | 3/2010 | Schultz | A61M 25/0147 604/95.04 |
| 2015/0366435 A1* | 12/2015 | Williams | A61B 1/0052 600/149 |

* cited by examiner

FIG. 1

PRIOR ART

PRIOR ART

STEERABLE CATHETER

TECHNICAL FIELD

The present disclosure relates to a catheter inserted into the human body or the like to be used for purpose of treatment, diagnosis, and the like.

BACKGROUND ART

In general, a catheter is a medical device that is inserted into the human body and the like to be used for the purpose of treatment, diagnosis, and the like.

It is important that such a catheter can be steered in the desired direction within the human body.

Figure 1:
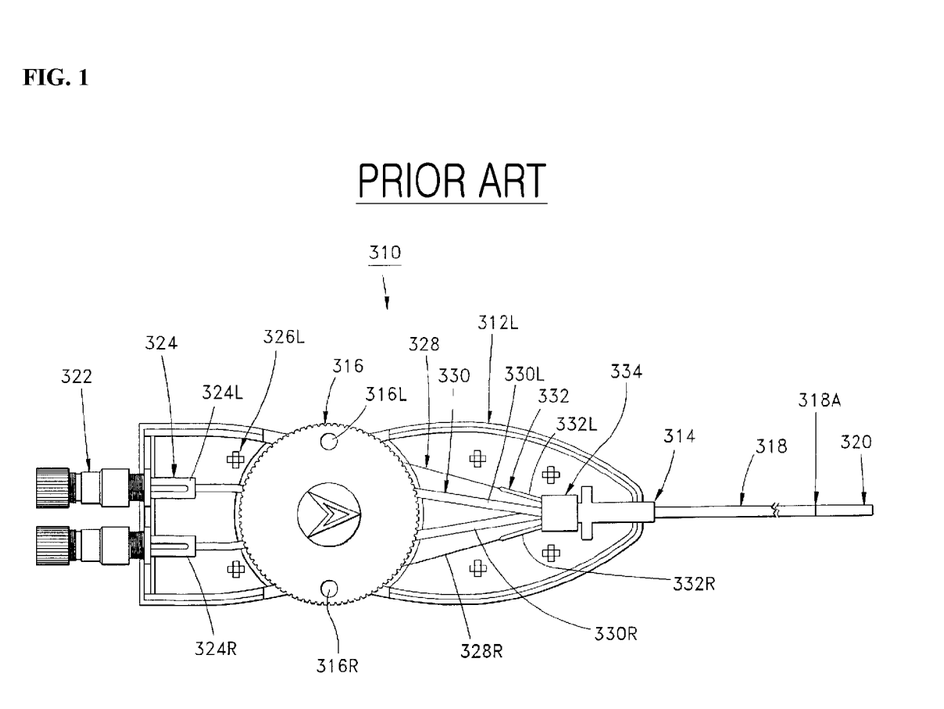
FIG. 1 is a view schematically showing a conventional steerable catheter.
Figure 2:
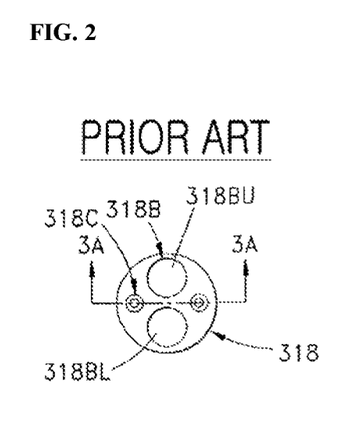
FIG. 2 is a cross-sectional view showing a lumen tip of the steerable catheter of FIG. 1.
Figure 3:
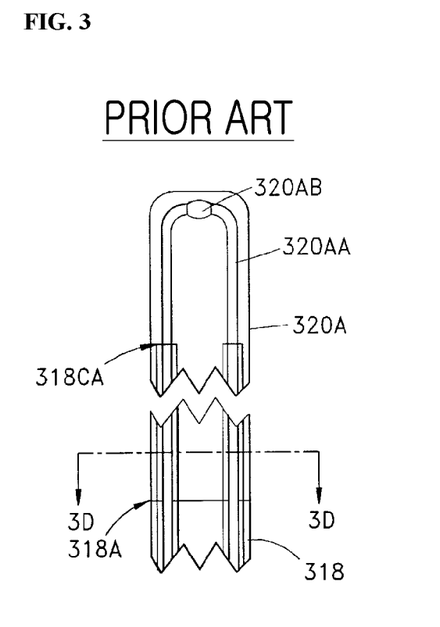
FIG. 3 is a view taken along the line 3A-3A of FIG. 2.

To this end, as related art, the steerable catheter disclosed in U.S. Pat. No. 6,030,360 provides, as shown in FIGS. 1 to 3, a technical configuration that includes a lumen shaft 318, a lumen tip 320 connected at the terminal end thereof through a connection 318A, two openings 318C formed longitudinally in the lumen shaft 318 and meeting each other at the lumen tip 320, a steering wire 328 in which one end is inserted into one opening and then exits from the other opening, and an attachment 318CA that secures the steering wire 328 to the terminal end of the lumen shaft 318. Accordingly, the lumen tip 320 may be steered in the left and right directions by pulling one end or pulling the other end of the steering wire 328.

However, since the conventional steerable catheter has a technical configuration of steering the lumen tip only in the left and right directions, in order to ensure that the lumen tip approaches the affected area accurately, it is necessary that the operator rotates the catheter properly to steer the lumen tip left and right while looking at the position of the lumen tip in three dimensions by using a separate C-type gantry based tomography apparatus and monitor. For this reason, there is a problem that the cost is increased because C-type gantry based tomography apparatus is additionally required, and also it is inconvenient to use and there is a high possibility of procedure failure because it is necessary to find the affected area while monitoring the image provided by the C-type gantry based tomography apparatus.

DETAILED DESCRIPTION OF INVENTION

Technical Problem

The technical problem of the present disclosure is to provide a steerable catheter, with which it is possible to enable a lumen tip approach an affected area only with an endoscope that is inserted together, and without the aid of a C-type gantry based tomography apparatus.

Solution to Problem

In order to achieve the objects mentioned above, a steerable catheter is provided, which may include a housing; a lumen shaft fixed to a front end of the housing; upper left, lower left, upper right and lower right wire parts provided respectively on upper left, lower left, upper right and lower right sides of inside of the lumen shaft to be slidable along a length direction thereof; upper left, lower left, upper right and lower right stoppers for respectively fixing the upper left, lower left, upper right and lower right wire parts to a terminal end of the lumen shaft; and a steering part for upwardly steering the terminal end of the lumen shaft by pulling the upper left and upper right wire parts, downwardly steering the terminal end of the lumen shaft by pulling the lower left and lower right wire parts, leftwardly steering the terminal end of the lumen shaft by pulling the upper left or lower left wire part, and rightwardly steering the terminal end of the lumen shaft by pulling the upper right or lower right wire part.

The lumen shaft may include upper left, lower left, upper right and lower right wire holes respectively extended on the upper left, lower left, upper right and lower right sides of the inside thereof in the longitudinal direction, in which the upper left, lower left, upper right and lower right wire parts may be provided by being slidably inserted in the upper left, lower left, upper right and lower right wire holes respectively.

According to the embodiment of the present disclosure described above, the steerable catheter may further include: a left connecting hole for connecting the upper left and lower left wire holes at the terminal end of the lumen shaft; and a right connection hole for connecting the upper right and lower right wire holes at the terminal end of the lumen shaft, in which the upper left and lower left wire parts may be formed of one left wire whose intermediate portion is placed in the left connection hole, and the upper right and lower right wire parts may be formed of one right wire whose intermediate portion is placed in the right connection hole.

The lumen shaft may include: a lumen shaft body fixed to the front end of the housing; and a lumen tip connected to the terminal end of the lumen shaft body through a connection part and forming the terminal end of the lumen shaft.

The steering part may include: a first handle pivotably provided on the housing by a first hinge shaft; an upper left wire fixing part provided at a left side portion of the first handle and fixing the tip of the upper left wire part; a lower right wire fixing part provided at a right side portion of the first handle and fixing the tip of the lower right wire part; a second handle pivotably provided on the housing by a second hinge shaft concentric with the first hinge shaft; an upper right wire fixing part provided at a left side portion of the second handle and fixing the tip of the upper right wire part; and a lower left wire fixing part provided at a right side portion of the second handle and fixing the tip of the lower left wire part.

When the first and second handles are rotated such that the left side portions of the first and second handles are backwardly moved, the upper left and upper right wire parts may be backwardly pulled and the lower right and lower left wire parts may be entered forward, such that the terminal end of the lumen shaft is upwardly steered, when the first and second handles are rotated such that the right side portions of the first and second handles may be backwardly moved, the lower right and lower left wire parts may be backwardly pulled and the upper left and upper right wire parts may be entered forward, such that the terminal end of the lumen shaft may be steered downward, when the first handle is rotated such that the left side portion of the first handle is backwardly moved, the upper left wire part may be backwardly pulled and the lower right wire part may be entered forward, such that the terminal end of the lumen shaft may be leftwardly steered, when the first handle is rotated such that the right side portion of the first handle is backwardly moved, the lower right wire part may be backwardly pulled and the upper left wire parts may be entered forward, such that the terminal end of the lumen shaft may be rightwardly steered, when the second handle is rotated such that the right side portion of the second handle is backwardly moved, the lower left wire part may be backwardly pulled and the upper right wire part may be entered forward, such that the terminal end of the lumen shaft may be leftwardly steered, and when the second handle is rotated such that the left side portion of the second handle is backwardly moved, the upper right wire part may be backwardly pulled and the lower left wire part may be entered forward, such that the terminal end of the lumen shaft may be rightwardly steered.

The steering part may further include a rotation stop unit which allows the first and second handles to be rotated when first force is applied and stops the rotation of the first and second handles when the first force is not applied.

The rotation stop unit may include: an elastic member provided between the first and the second handles and applying a force in a direction in which the first and second handles are distanced away from each other; a plurality of first locking grooves provided on a surface of the first handle facing the housing; a plurality of first locking protrusions provided on the housing to correspond to the plurality of first locking grooves; a plurality of second locking grooves provided on a surface of the second handle facing the housing; and a plurality of second locking protrusions provided on the housing to correspond to the plurality of second locking grooves.

The steerable catheter may further include first and second instrument insertion holes formed in the inside of the lumen shaft in the length direction thereof, in which the first and second instrument insertion holes may have different diameters from each other.

The lumen shaft may have an outer diameter of 3.2 mm, the first instrument insertion hole may have an inner diameter of 1.5 mm, and the second instrument insertion hole may have an inner diameter of 1.2 mm.

Effects of the Invention

As described above, the steerable catheter according to an embodiment of the present disclosure may have the following effects.

According to one embodiment of the present disclosure, there is provided a technical configuration that includes a housing, a lumen shaft, upper left, lower left, upper right and lower right wire parts, upper left, lower left, upper right and lower right stoppers, and a steering part, in which the steering part upwardly steers the terminal end of the lumen shaft by pulling the upper left and upper right wire parts, downwardly steers the terminal end of the lumen shaft by pulling the lower left and lower right wire parts, leftwardly steers the terminal end of the lumen shaft by pulling the upper left or lower left wire part, and rightwardly steers the terminal end of the lumen shaft by pulling the upper right or lower right wire part, so that the terminal end of the lumen shaft can be steered in four directions, thereby enabling the terminal end of the lumen shaft to approach the affected area only with the aid of an endoscope that is inserted into the catheter according to the present disclosure. As a result, there is no need for a C-type gantry based tomography apparatus, which is otherwise used together in the related art, thereby reducing costs, and also there is no need to monitor the image provided by the C-type gantry based tomography apparatus, which may increase convenience of use.

DETAILED DESCRIPTION

Hereinafter, preferred embodiments of the present disclosure will be described in detail with reference to the accompanying drawings. However, the description proposed herein is not intended to limit the scope of the disclosure, so it should be understood that other equivalents and modifications could be made thereto without departing from the scope of the disclosure.

Figure 4:
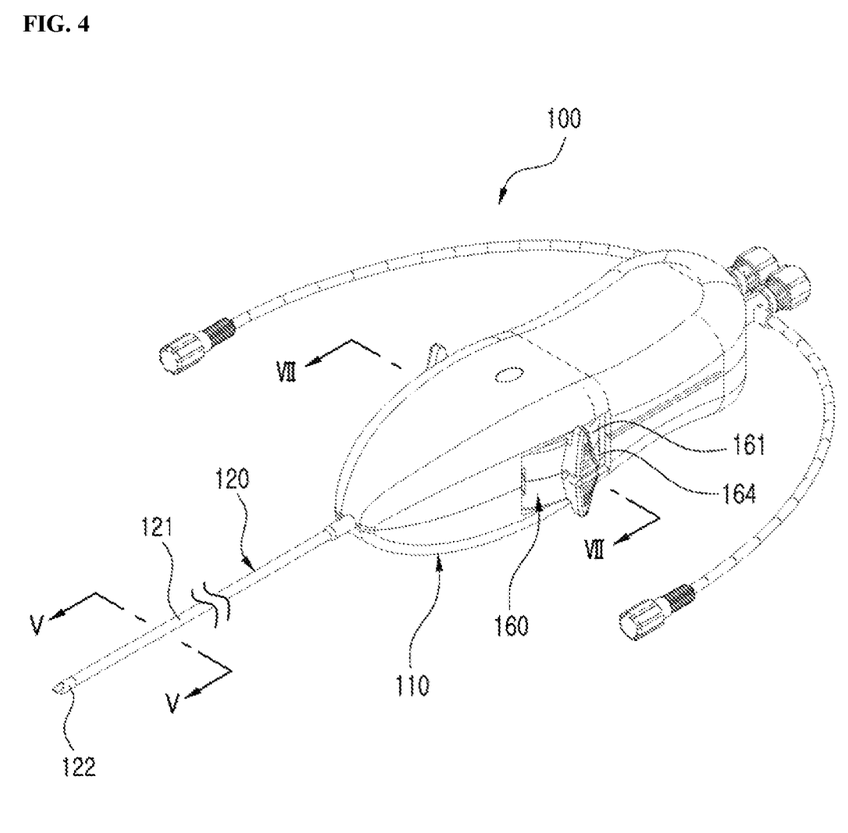
FIG. 4 is a perspective view schematically showing a steerable catheter according to an embodiment of the present disclosure.
Figure 5:
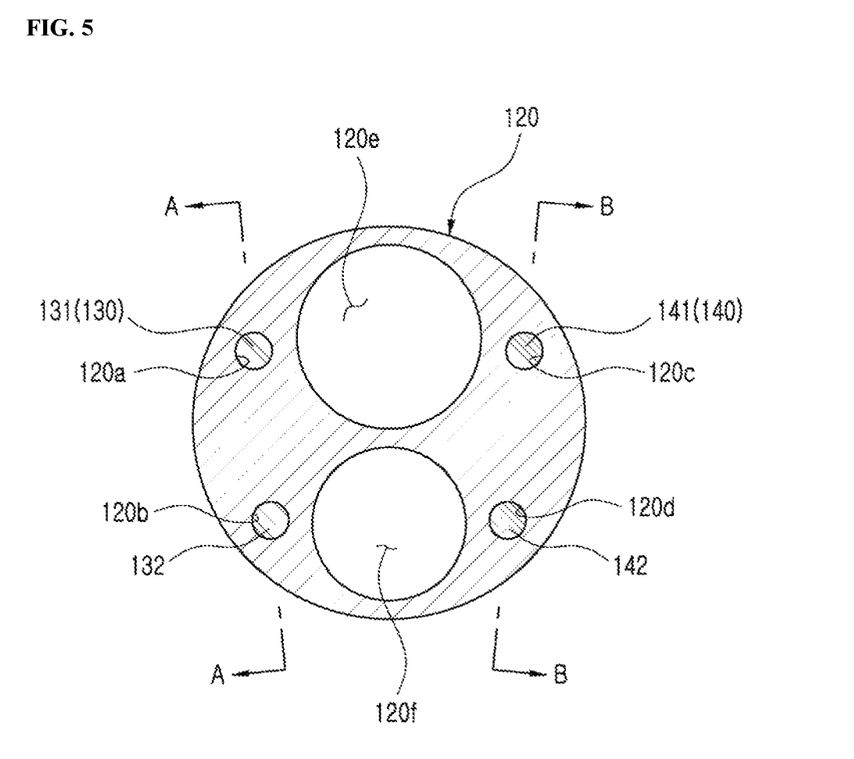
FIG. 5 is a view showing the steerable catheter of FIG. 4 taken along line V-V.
Figure 6A:
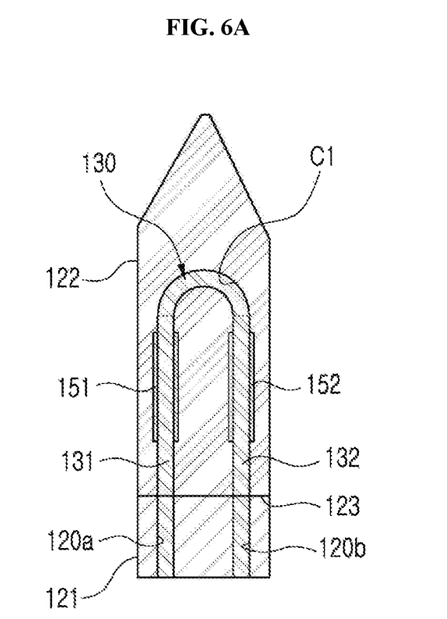
FIG. 6A is a view showing the lumen shaft of FIG. 5 taken along line A-A and FIG. 6B is a view showing the lumen shaft of FIG. 5 taken along line B-B.
Figure 6B:
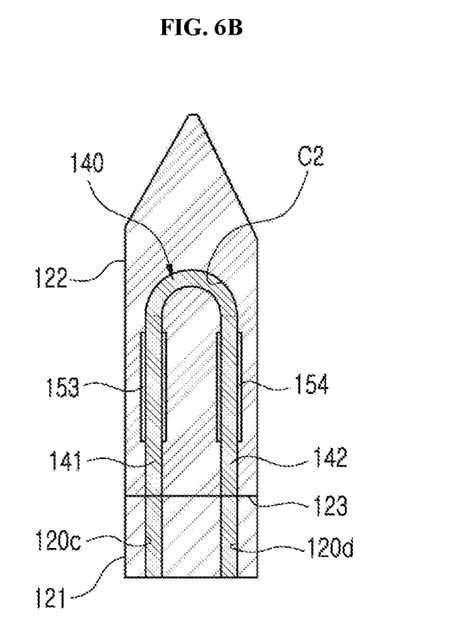

FIG. 4 is a perspective view schematically showing a steerable catheter according to an embodiment of the present disclosure, FIG. 5 is a view showing the steerable catheter of FIG. 4 taken along line V-V, FIG. 6A is a view showing the lumen shaft of FIG. 5 taken along line A-A and FIG. 6B is a view showing the lumen shaft of FIG. 5 taken along line B-B.

Figure 7:
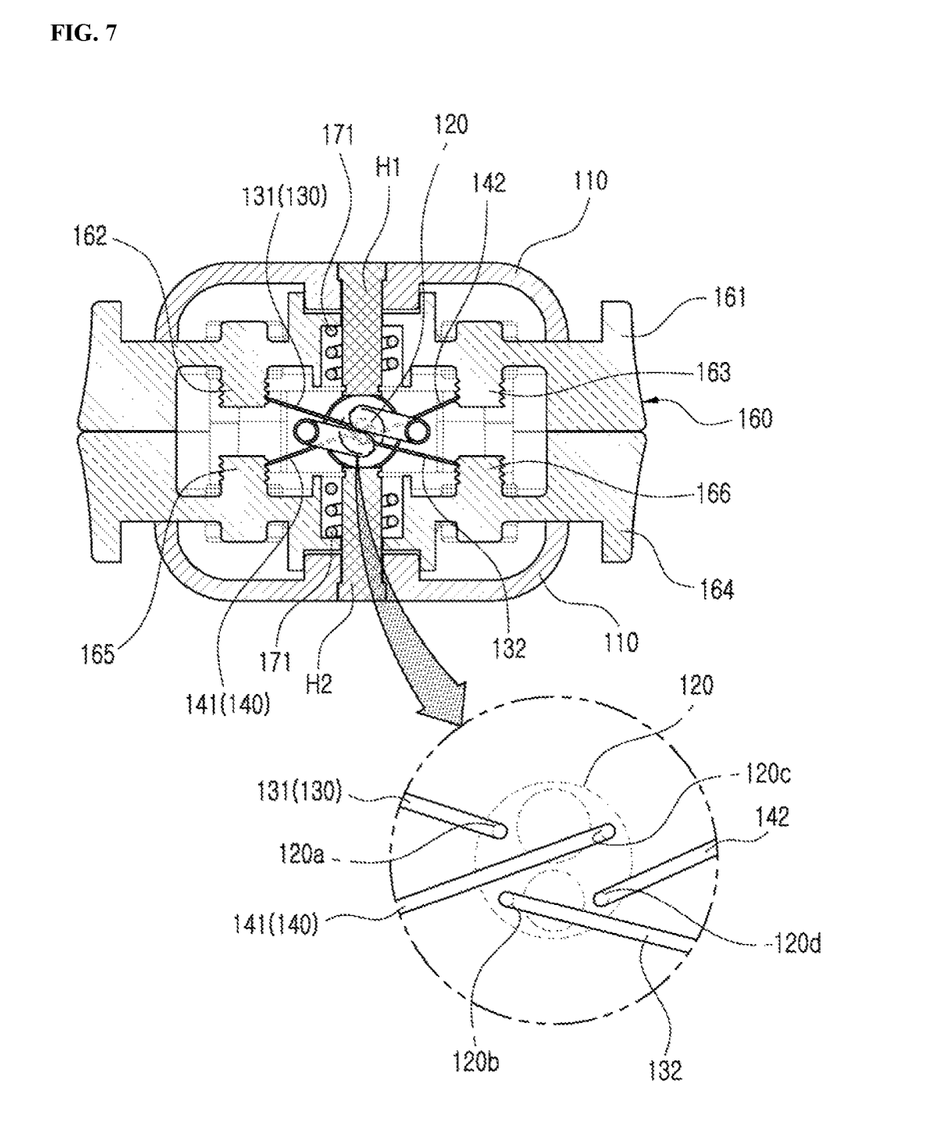
FIG. 7 is a view showing the steerable catheter of FIG. 4 taken along line VII-VII.
Figure 8:
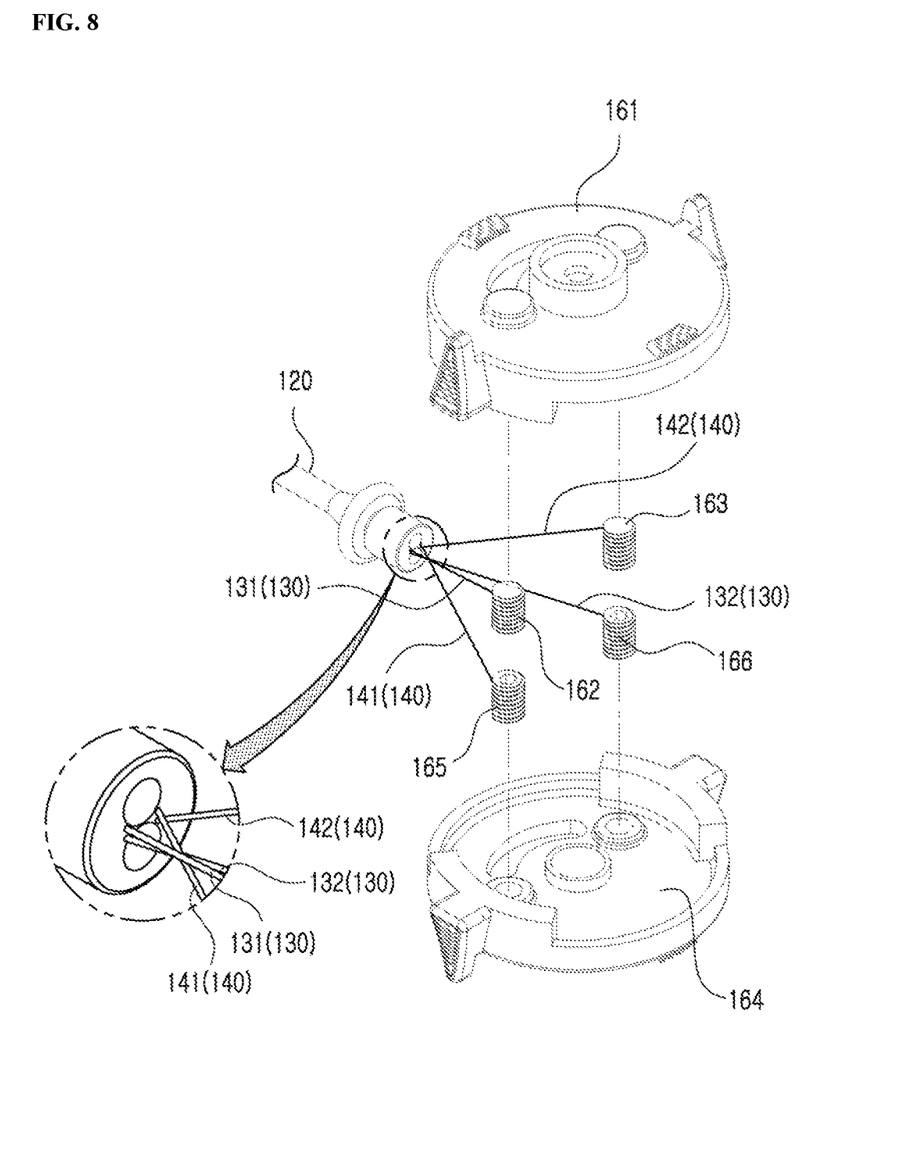
FIG. 8 is an exploded perspective view for schematically showing the steering part of FIG. 7.
Figure 9:
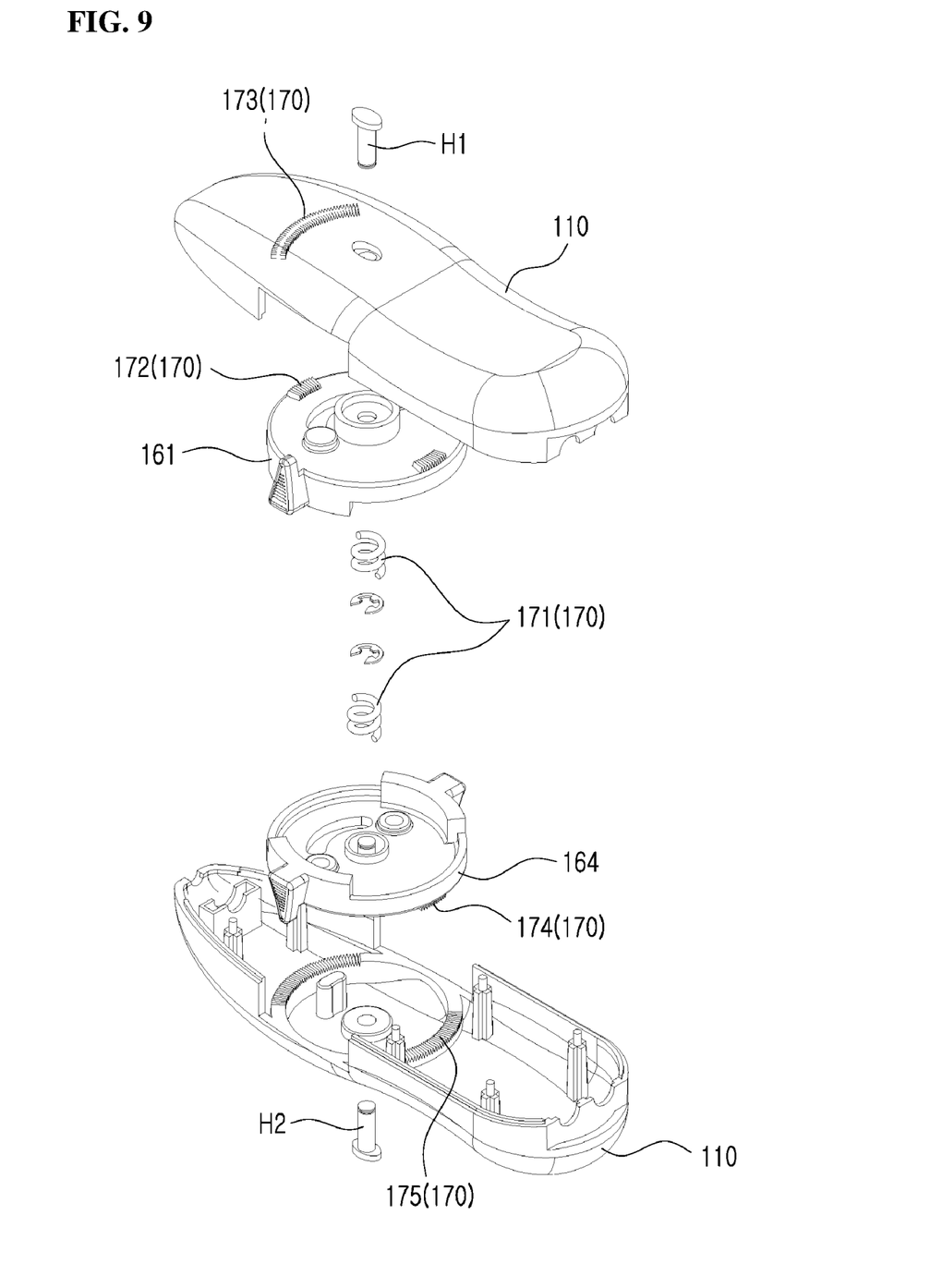
FIG. 9 is an exploded perspective view for schematically showing a rotation stop unit of the steerable catheter of FIG. 4.
Figure 10:
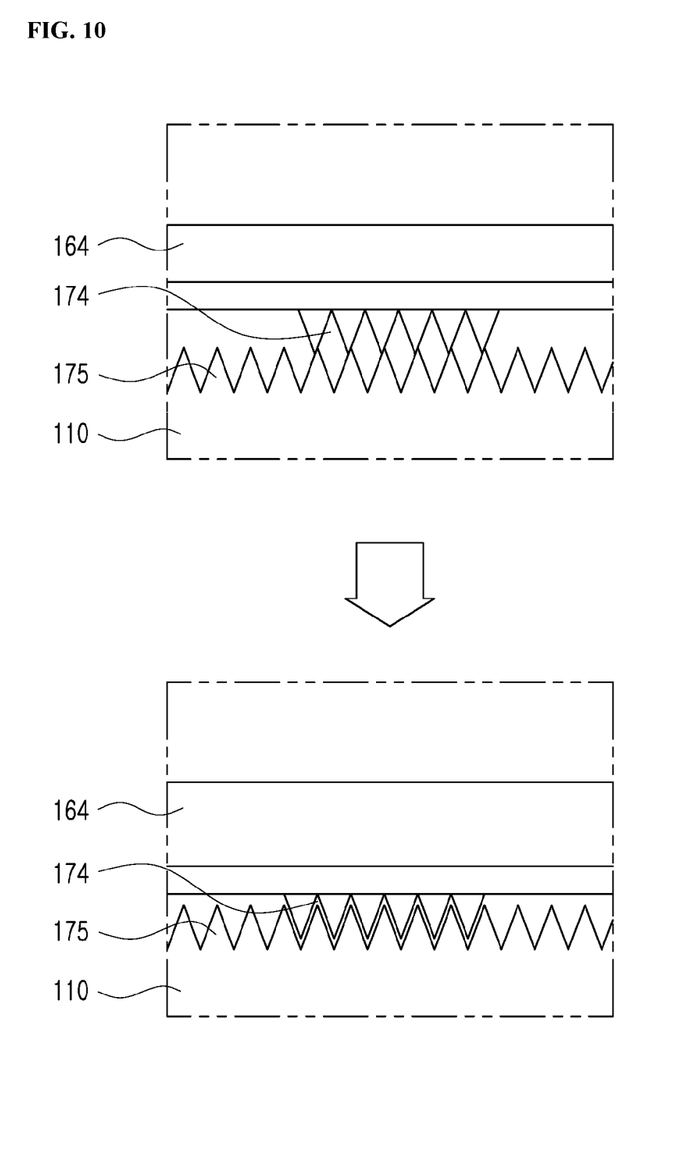
FIG. 10 is a main view sequentially illustrating a process of rotating a second handle and a process of stopping the second handle.

FIG. 7 is a view showing the steerable catheter of FIG. 4 taken along line VII-VII, FIG. 8 is an exploded perspective view for schematically showing the steering part of FIG. 7, FIG. 9 is an exploded perspective view for schematically showing a rotation stop unit of the steerable catheter of FIG. 4, and FIG. 10 is a main view sequentially illustrating a process of rotating the second handle and a process of stopping the second handle.

As shown in FIGS. 4 to 10, the steering catheter 100 according to an embodiment of the present disclosure includes a housing 110, a lumen shaft 120, upper left, lower left, upper right and lower right wire parts 131, 132, 141, and 142, upper left, lower left, upper right and lower right stoppers 151, 152, 153, and 154, and a steering part 160. Hereinafter, each of the components will be described in detail with continued reference to FIGS. 4 to 10.

The housing 110 is a component that the operator may hold by hand to manipulate the steering part 160 and the like, and as shown in FIGS. 4 and 7, may include a built-in steering part 160 and the lumen shaft 120 fixed to the tip thereof. As shown in FIG. 9, the housing 110 may have a structure in which upper and lower portions thereof are separable from each other.

The lumen shaft 120 is a component for guiding a surgical instrument (not shown) and the like into the body and may be fixed to the front end of the housing 110 as shown in FIG. 4.

For example, as shown in FIG. 5, the lumen shaft 120 may include upper left, lower left, upper right and lower right wire holes 120a, 120b, 120c, and 120d. In particular, as shown in FIG. 6, the upper left, lower left, upper right and lower right wire holes 120*a*, 120*b*, 120*c*, and 120*d* may be respectively extended on the upper left, lower left, upper right and lower right sides of the inside of the lumen shaft 120 in the longitudinal direction thereof.

As shown in FIG. 6, a left connecting hole C1 and a right connecting hole C2 may be further formed inside of the terminal end of the lumen shaft 120. The left connecting hole C1 is a component for connecting the upper left and lower left wire holes 120*a* and 120*b* to each other at the terminal end of the lumen shaft 120, and the right connecting hole C2 is component for connecting the upper right and lower right wire holes 120*c* and 120*d* to each other at the terminal end of the lumen shaft 120.

In addition, the lumen shaft 120 may include, as shown in FIGS. 4 and 6, a lumen shaft body 121 fixed to the front end of the housing 110, and a lumen tip 122 connected at the terminal of the lumen shaft body 121 through the connecting portion 123 and forming the terminal end of the lumen shaft 120.

Furthermore, as shown in FIG. 5, first and second instrument insertion holes 120*e* and 120*f* may be further formed inside the lumen shaft 120 in the length direction thereof, and the first and second instrument insertion holes 120*e* and 120*f* may have different diameters from each other. For example, the lumen shaft 120 may have an outer diameter of approximately 3.2 mm, the first instrument insertion hole 120*e* may have an inner diameter of approximately 1.5 mm, and the second instrument insertion hole 120*f* may have an inner diameter of approximately 1.2 mm. For reference, when the outer diameter of the lumen shaft 120 is greater than 3.2 mm, it may be difficult to enter the epidural space. Accordingly, while maintaining the outer diameter (3.2 mm) of the lumen shaft 120 as it is, the inner diameter of the first instrument insertion hole 120*e* may be extended to 1.5 mm to thereby allow the instrument (not shown) such as forceps to be easily inserted. The upper left, lower left, upper right and lower right wire parts 131, 132, 141, and 142 are the components that, together with the steering part 160, steer the direction of the lumen tip 122, and may be provided respectively on the upper left, lower left, upper right and lower right sides of the inside of the lumen shaft 120 so as to be slidable along its length direction as shown in FIGS. 5 and 6. For example, as shown in FIGS. 5 and 6, when the lumen shaft 120 includes the upper left, lower left, upper right and lower right wire holes 120*a*, 120*b*, 120*c* and 120*d*, the upper and lower left, upper right and lower right wire parts 131, 132, 141 and 142 may be provided by being slidably inserted in the upper left, lower left, upper right and lower right wire holes 120*a*, 120*b*, 120*c* and 120*d*, respectively.

Furthermore, as shown in FIG. 6, when the left connecting hole C1 for connecting the upper left and lower left wire holes 120*a* and 120*b* at the terminal end of the lumen shaft 120, and the right connection hole C2 for connecting the upper right and lower right wire holes 120*c* and 120*d* at the terminal end of the lumen shaft 120 are further provided, the upper left and lower left wire parts 131 and 132 may be formed of one left wire 130 with a portion of the left wire 130 between the upper left and lower left wire parts 131 and 132 being positioned in the left connection hole C1, and the upper right and lower right wire parts 141 and 142 may be formed of one right wire 140 with a portion of the right wire 140 between the upper right and lower right wire parts 141 and 142 being positioned in the right connection hole C2.

As shown in FIG. 6, the upper left, lower left, upper right and lower right stoppers 151, 152, 153 and 154 are components for fixing the upper left, lower left, upper right and lower right wire parts 131, 132, 141 and 142 to the terminal end of the lumen shaft 120, respectively.

The steering part 160 may upwardly steer the terminal end of the lumen shaft 120 by pulling the upper left and upper right wire parts 131 and 141, downwardly steer the terminal end of the lumen shaft 120 by pulling the lower left and lower right wire parts 132 and 142, leftwardly steer the terminal end of the lumen shaft 120 by pulling the upper left or lower left wire parts 131 or 132, and rightwardly steer the terminal end of the lumen shaft 120 by pulling the upper right or lower right wire part 141 or 142.

For example, the steering part 160 may include a first handle 161, an upper left wire fixing part 162, a lower right wire fixing part 163, a second handle 164, an upper right wire fixing part 165, and a lower left wire fixing part 166, as shown in FIGS. 7 and 8.

The first handle 161 may be pivotably provided at the housing 110 by the first hinge shaft H1, the upper left wire fixing part 162 may be provided at the left side portion of the first handle 161 and the tip of the upper left wire part 131 may be fixed thereto, and the lower right wire fixing part 163 may be provided at a right side portion of the first handle 161 and the tip of the lower right wire part 142 may be fixed thereto. The second handle 164 may be pivotably provided on the housing 110 by a second hinge shaft H2 concentric with the first hinge shaft H1, the upper right wire fixing part 165 may be provided at the left side portion of the second handle 164 and the tip of the upper right wire part 141 may be fixed thereto, and the lower left wire fixing part 166 may be provided at a right side portion of the second handle 164 and the tip of the lower left wire part 132 may be fixed thereto.

Therefore, as shown in FIGS. 7 and 8, when the first and second handles 161 and 164 are rotated such that the left side portions of the first and second handles 161 and 164 are backwardly moved, the upper left and upper right wire parts 131 and 141 are backwardly pulled and the lower right and lower left wire parts 142 and 132 are entered forward, such that the lumen tip 122 may be upwardly steered, and when the first and second handles 161 and 164 are rotated such that the right side portions of the first and second handles 161 and 164 are backwardly moved, the lower left and lower right wire parts 132 and 142 are backwardly pulled and the upper left and upper right wire parts 131 and 141 are entered forward, such that the lumen tip 122 may be downwardly steered. In addition, when the first handle 161 is rotated such that the left side portion of the first handle 161 is backwardly moved, the upper left wire part 131 is backwardly pulled and the lower right wire part 142 is entered forward, such that the lumen tip 122 may be leftwardly steered, and when the first handle 161 is rotated such that the right side portion of the first handle 161 is backwardly moved, the lower right wire part 142 is backwardly pulled and the upper left wire part 131 is entered forward, such that the lumen tip 122 may be rightwardly steered. Further, when the second handle 164 is rotated such that the right side portion of the second handle 164 is backwardly moved, the lower left wire part 132 is backwardly pulled and the upper right wire part 141 is entered forward, such that the lumen tip may be leftwardly steered, and when the second handle 164 is rotated such that the left side portion of the second handle 164 is backwardly moved, the upper right wire part 141 is backwardly pulled and the lower left wire part 132 is entered forward, the lumen tip 122 may be rightwardly steered.

In addition, as shown in FIGS. 9 and 10, the adjusting unit 160 may further include a rotation stop unit 170 to allow the first and second handles 161 and 164 to be rotated when the first force is applied, and stop the rotation of the first and second handles 161 and 164 when the first force is not applied.

For example, as shown in FIG. 9, the rotation stop unit 170 may include an elastic member 171, a plurality of first locking grooves 172, a plurality of first locking protrusions 173, a plurality of second locking grooves 174, and a plurality of second locking protrusions 175.

The elastic member 171 may be provided between the first handle 161 and the second handle 164 to apply a force in a direction to move the first and second handles 161 and 164 away from each other, and the plurality of first locking grooves 172 may be provided on a surface of the first handle 161 facing the housing 110, and the plurality of first locking protrusions 173 may be provided on the housing 110 to correspond to the plurality of first locking grooves 172. The plurality of second locking grooves 174 may be provided on a surface of the second handle 164 facing the housing 110, and the plurality of second locking protrusions 175 may be provided on the housing 110 to correspond to the plurality of second locking grooves 174. Furthermore, the elastic force of the elastic member 171 may be designed to be smaller than the first force such that the elastic member 171 can be compressed when the first force is applied.

Accordingly, as shown in FIG. 10, when a rotational force of the first force is applied to the second handle 164, the plurality of second locking grooves 174 of the second handle 164 are separated from the plurality of second locking protrusions 175 of the housing 110 to a rotatable state and also to a desired position, such that, when the first force applied is removed, the rotation of the second handle 164 may be stopped as the plurality of second locking grooves 174 of the second handle 164 are engaged with the plurality of second locking protrusions 175 of the housing 110.

While the present disclosure has been described in detail, it should be understood that the detailed description and specific examples, while indicating preferred embodiments of the disclosure, are given by way of illustration only, since various changes and modifications within the scope of the disclosure will become apparent to those skilled in the art from this detailed description.

INDUSTRIAL APPLICABILITY

Since the present disclosure relates to a catheter inserted into the human body or the like and used for purpose of treatment, diagnosis, and the like, which is industrially applicable.

What is claimed is:

1. A steerable catheter comprising:
   a housing;
   a lumen shaft fixed to a front end of the housing;
   upper left, lower left, upper right and lower right wire parts provided respectively on upper left, lower left, upper right and lower right sides of inside of the lumen shaft to be slidable along a length direction thereof;
   upper left, lower left, upper right and lower right stoppers for respectively fixing the upper left, lower left, upper right and lower right wire parts to a terminal end of the lumen shaft; and
   a steering part for upwardly steering the terminal end of the lumen shaft by pulling the upper left and upper right wire parts,
   downwardly steering the terminal end of the lumen shaft by pulling the lower left and lower right wire parts,
   leftwardly steering the terminal end of the lumen shaft by pulling the upper left or lower left wire part, and
   rightwardly steering the terminal end of the lumen shaft by pulling the upper right or lower right wire part,
   wherein the steering part includes:
   a first handle pivotably provided on the housing by a first hinge shaft;
   a second handle pivotably provided on the housing by a second hinge shaft concentric with the first hinge shaft; and
   a rotation stop unit which allows the first and second handles to be rotated when first force is applied and stops the rotation of the first and second handles when the first force is not applied, and
   wherein the rotation stop unit includes:
   an elastic member provided between the first and the second handles and applying a force in a direction in which the first and second handles are distanced away from each other;
   a plurality of first locking grooves provided on a surface of the first handle facing the housing;
   a plurality of first locking protrusions provided on the housing to correspond to the plurality of first locking grooves;
   a plurality of second locking grooves provided on a surface of the second handle facing the housing; and
   a plurality of second locking protrusions provided on the housing to correspond to the plurality of second locking grooves.

2. The steerable catheter according to claim 1, wherein the lumen shaft includes upper left, lower left, upper right and lower right wire holes respectively extended on the upper left, lower left, upper right and lower right sides of the inside thereof in a longitudinal direction,
   wherein the upper left, lower left, upper right and lower right wire parts are provided by being slidably inserted in the upper left, lower left, upper right and lower right wire holes respectively.

3. The steerable catheter according to claim 2, wherein the steerable catheter further includes:
   a left connecting hole for connecting the upper left and lower left wire holes at the terminal end of the lumen shaft; and
   a right connection hole for connecting the upper right and lower right wire holes at the terminal end of the lumen shaft,
   wherein the upper left and lower left wire parts are formed of one left wire whose intermediate portion is placed in the left connection hole, and
   the upper right and lower right wire parts are formed of one right wire whose intermediate portion is placed in the right connection hole.

4. The steerable catheter according to claim 3, wherein the lumen shaft includes:
   a lumen shaft body fixed to the front end of the housing; and
   a lumen tip connected to the terminal end of the lumen shaft body through a connection part and forming the terminal end of the lumen shaft.

5. The steerable catheter according to claim 2, further including first and second instrument insertion holes formed in the inside of the lumen shaft in the length direction thereof, wherein the first and second instrument insertion holes have different diameters from each other.

6. The steerable catheter according to claim 5, wherein the lumen shaft has an outer diameter of 3.2 mm, the first instrument insertion hole has an inner diameter of 1.5 mm, and the second instrument insertion hole has an inner diameter of 1.2 mm.

7. The steerable catheter according to claim 1, wherein the steering part includes:
- an upper left wire fixing part provided at a left side portion of the first handle and fixing a tip of the upper left wire part;
- a lower right wire fixing part provided at a right side portion of the first handle and fixing a tip of the lower right wire part;
- an upper right wire fixing part provided at a left side portion of the second handle and fixing a tip of the upper right wire part; and
- a lower left wire fixing part provided at a right side portion of the second handle and fixing a tip of the lower left wire part.

8. The steerable catheter according to claim 7, wherein, when the first and second handles are rotated such that the left side portions of the first and second handles are backwardly moved, the upper left and upper right wire parts are backwardly pulled and the lower right and lower left wire parts are entered forward, such that the terminal end of the lumen shaft is upwardly steered, when the first and second handles are rotated such that the right side portions of the first and second handles are backwardly moved, the lower right and lower left wire parts are backwardly pulled and the upper left and upper right wire parts are entered forward, such that the terminal end of the lumen shaft is steered downward, when the first handle is rotated such that the left side portion of the first handle is backwardly moved, the upper left wire part is backwardly pulled and the lower right wire part is entered forward, such that the terminal end of the lumen shaft is leftwardly steered, when the first handle is rotated such that the right side portion of the first handle is backwardly moved, the lower right wire part is backwardly pulled and the upper left wire part is entered forward, such that the terminal end of the lumen shaft is rightwardly steered, when the second handle is rotated such that the right side portion of the second handle is backwardly moved, the lower left wire part is backwardly pulled and the upper right wire part is entered forward, such that the terminal end of the lumen shaft is leftwardly steered, and when the second handle is rotated such that the left side portion of the second handle is backwardly moved, the upper right wire part is backwardly pulled and the lower left wire part is entered forward, such that the terminal end of the lumen shaft is rightwardly steered.

\* \* \* \* \*